(12) United States Patent
Fanda et al.

(10) Patent No.: US 9,682,081 B2
(45) Date of Patent: Jun. 20, 2017

(54) PHARMACEUTICAL GASTRO-RETENTIVE SOLID ORAL DOSAGE FORM OF NILOTINIB

(71) Applicant: SUN PHARMACEUTICAL INDUSTRIES LIMITED, Mumbai, Maharashtra (IN)

(72) Inventors: Anuj Kumar Fanda, Ghaziabad (IN); Ravish Sharma, Khargone (IN); Kumaravel Vivek, Chennai (IN); Lalit Kumar Khurana, Chandigarh (IN); Shavej Ahmad, Lucknow (IN); Romi Barat Singh, Varanasi (IN); Ajay Kumar Singla, Gurgaon (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 14/787,167

(22) PCT Filed: Apr. 25, 2014

(86) PCT No.: PCT/IB2014/061018
§ 371 (c)(1),
(2) Date: Oct. 26, 2015

(87) PCT Pub. No.: WO2014/174496
PCT Pub. Date: Oct. 30, 2014

(65) Prior Publication Data
US 2016/0106748 A1   Apr. 21, 2016

(30) Foreign Application Priority Data
Apr. 25, 2013   (IN) .......................... 1227/DEL/2013

(51) Int. Cl.
| | | |
|---|---|---|
| *A61K 31/445* | (2006.01) | |
| *A61K 9/20* | (2006.01) | |
| *A61K 9/24* | (2006.01) | |
| *A61K 9/28* | (2006.01) | |
| *A61K 31/506* | (2006.01) | |
| *A61K 9/00* | (2006.01) | |
| *A61K 9/48* | (2006.01) | |

(52) U.S. Cl.
CPC .......... *A61K 31/506* (2013.01); *A61K 9/0004* (2013.01); *A61K 9/0065* (2013.01); *A61K 9/20* (2013.01); *A61K 9/4891* (2013.01)

(58) Field of Classification Search
CPC .. A61K 31/445; A61K 9/2054; A61K 9/0004; A61K 9/2866
USPC .......................... 514/326; 424/465, 473, 474
See application file for complete search history.

(56) References Cited

U.S. PATENT DOCUMENTS

| | | | |
|---|---|---|---|
| 7,169,791 B2 | 1/2007 | Breitenstein et al. | ........ 514/275 |
| 8,293,756 B2 | 10/2012 | Bruneau | ....................... 514/275 |

FOREIGN PATENT DOCUMENTS

| | | | | |
|---|---|---|---|---|
| WO | WO 01/37812 | 5/2001 | ............... | A61K 9/20 |
| WO | WO 02/102415 | 12/2002 | ............... | A61K 47/38 |
| WO | WO 2010/035273 | 4/2010 | ............... | A61K 9/20 |
| WO | WO 2011/048494 | 4/2011 | ............... | A61K 9/24 |

*Primary Examiner* — Raymond Henley, III

(57) ABSTRACT

The present invention relates to a pharmaceutical gastro-retentive solid oral dosage form comprising nilotinib as the active ingredient. The invention is further related to methods of preparing said dosage form.

10 Claims, No Drawings

PHARMACEUTICAL GASTRO-RETENTIVE SOLID ORAL DOSAGE FORM OF NILOTINIB

CROSS REFRENCE TO RELATED APPLICATIONS

This application is a national phase application of PCT patent application no. PCT/IB2014/061018 having International Filing Date of Apr. 25, 2014, which claims the benefit of the filing date of Indian provisional application no. 1227/DEL/2013 filed on Apr. 25, 2013, the disclosure of which is hereby incorporated by reference.

FIELD OF THE INVENTION

The present invention relates to a pharmaceutical gastro-retentive solid oral dosage form comprising nilotinib as the active ingredient. The invention is further related to methods of preparing said solid oral dosage form.

BACKGROUND OF THE INVENTION

Nilotinib was first disclosed in U.S. Pat. No. 7,169,791. It is chemically described as 4-methyl-N-[3-(4-methyl-1H-imidazol-1-yl)-5-(trifluoromethyl)phenyl]-3-[[4-(3-pyridinyl)-2-pyrimidinyl]amino]-benzamide and is an inhibitor of the protein tyrosine kinase (TK) activity of BCR-ABL.

U.S. Pat. No. 8,293,756 discloses pharmaceutical compositions of nilotinib prepared by wet granulation.

Nilotinib is characterized as a Class IV compound according to the Biopharmaceutical Classification System (BCS), which means that it has low/moderate aqueous solubility and low permeability. The solubility of nilotinib at 25° C. in aqueous solutions decreases strongly with increasing pH and it is practically insoluble at pH 4.5 and higher. This decrease in the solubility of nilotinib in environments with a pH of more than 1 leads to a decrease in the absorption of nilotinib. The poor water-solubility of nilotinib and its salts mean that they are difficult to formulate as oral delivery dosage forms with good bioavailability. Hence, there is a need to develop a pharmaceutical solid oral dosage form of nilotinib which has better solubility and bioavailability. In the present invention, the inventors have developed such a pharmaceutical oral solid dosage form of nilotinib.

SUMMARY OF THE INVENTION

In one general aspect, the present invention provides a gastro-retentive solid oral dosage form which comprises nilotinib or a salt thereof, at least one rate controlling polymer, and other pharmaceutically acceptable excipients.

In an embodiment of the above aspect, the rate controlling polymer is a swelling agent.

In another embodiment of the above aspect, the dosage form may further comprise an acidifying agent.

In another embodiment of the above aspect, the dosage form may be administered once daily or twice daily.

In another embodiment of the above aspect, the dosage form is a tablet. The gastro-retentive action of the tablet is based on one or more mechanisms, for example, floatation, gas generation, or swelling.

In another embodiment of the above aspect, the dosage form may further comprise one or more osmogen agents.

In another embodiment of the above aspect, the other pharmaceutically acceptable excipients are selected from the group comprising diluents, matrix forming agents, disintegrants, binding agents, gas-generating agents, semi-permeable film-forming agents, glidants, and lubricants.

The details of the various embodiments of the invention are set forth in the description below. Other features and advantages of the invention will also be apparent from the description.

DETAILED DESCRIPTION OF THE INVENTION

The term "gastro-retentive", as used herein, refers to a pharmaceutical dosage form which is capable of staying in the stomach for a prolonged period of time, preferably for a period longer than that of food, and therefore is capable of releasing the active ingredient in the stomach for a time period longer than when delivered as a conventional dosage form. The gastro-retentive time may be characterized by retention of the dosage form in the stomach for a period that is longer than the normal emptying time of the stomach, i.e., longer than about 2 hours.

Several mechanisms for gastro-retentive action of the oral solid dosage form may be designed and developed by applying approaches which include low-density floating systems that cause buoyancy in gastric fluid; high-density sinking systems that are retained in the bottom of the stomach; mucoadhesive systems that cause bioadhesion to stomach mucosa; gas generation by the dosage form that causes buoyancy in gastric fluid; swelling of the dosage form beyond the size which can pass through the human pyloric sphincter of the stomach; and large sized dosage forms per se which may limit passing of the dosage form through the pyloric sphincter. The diameter of the human pyloric sphincter is on an average 12 mm (±7 mm) and therefore a dosage form larger than the pyloric diameter cannot pass through the stomach.

The term "solid oral dosage form", as used herein, includes tablets, mini-tablets, capsules, caplets, granules, beads, pellets, multiparticulates, spheroids, or combinations thereof. If the solid form is a tablet, the tablet can be of any suitable shape, such as round, spherical, oval, concave, bi-concave, hemispherical, or any polygonal shape, such as square, rectangular, pentagonal, hexagonal, and the like. The tablet may have a monolithic or a multilayer structure.

The term "rate-controlling polymer", as used herein, refers to polymers which are capable of controlling the release of the active ingredient from the dosage form. The polymer can control the release of the active ingredient by any mechanism, such as swelling, matrix forming, or film forming.

The term "swelling agent", as used herein, refers to polymers which are capable of absorbing water, resulting in physical swelling and expansion. The swelling of the polymer can be characterized by an increase in the dimensions of the dosage form in one or more directions. Preferred examples of swelling agents include, but are not limited to, hypromellose, methyl cellulose, hydroxypropyl cellulose, hydroxyethyl cellulose, carboxymethyl cellulose, guar gum, xanthan gum, tragacanth gum, carrageenan, pectin, egg albumin, chitosan, pectin, bovine serum albumin, microcrystalline cellulose, cross-linked carboxymethyl cellulose, cross-linked polyvinyl pyrrolidone, or a starch.

The term "acidifying agent", as used herein, refers to substances which are able to create an acidic pH environment within and around the dosage form and therefore increase the solubility and dissolution of the active ingredients which are soluble in acidic pH. Preferred examples of acidifying agents include, but are not limited to, fumaric acid, citric acid, tartaric acid, amino acid, or lactic acid.

Preferred examples of osmogen agents include, but are not limited to, organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, sorbitol, other similar or equivalent materials, and combinations thereof.

Preferred examples of diluents include, but are not limited to, calcium phosphate-dibasic, calcium carbonate, lactose, glucose, microcrystalline cellulose, cellulose powdered, silicified microcrystalline cellulose, calcium silicate, starch, starch pregelatinized, and polyols such as mannitol, sorbitol, xylitol, maltitol, and sucrose.

The term "matrix forming agent", as used herein, refers to the pharmaceutical agents which impart structural integrity and provide mechanical strength to the dosage form, among other functions. Preferred examples of matrix forming agents include, but are not limited to, hydroxypropyl methylcellulose (HPMC), acrylic acid polymers, polyvinyl acetate (PVA), polyvinylpyrrolidone (PVP), cross-linked polyvinylpyrrolidone, ethylcellulose, carbomer homopolymer (type A), and combinations thereof.

Preferred examples of disintegrants include, but are not limited to, cross-linked cellulose, cross-linked polyvinylpyrrolidone (crospovidone), sodium starch glycolate, polyvinylpyrrolidone (polyvidone, povidone), sodium carboxymethylcellulose, cross-linked sodium carboxymethylcellulose (croscarmellose sodium), hydroxypropyl cellulose, hydroxypropyl methylcellulose, xanthan gum, alginic acid, and soy polysaccharides.

Preferred examples of binding agents include, but are not limited to, starch, pregelatinized starch, carboxymethyl cellulose, sodium cellulose, microcrystalline cellulose, hydroxypropyl cellulose, hydroxypropyl methylcellulose, polyvinylpyrrolidone, crospovidone, and combinations thereof.

Preferred examples of gas-generating agents include, but are not limited to, alkali metal carbonates and bicarbonates such as sodium bicarbonate and calcium carbonate. When gas-generating agents come in contact with water or stomach acid, they generate gas bubbles which help keep the dosage form in a buoyant state and hence avoid its passage through the stomach.

The term "semi-permeable film", as used herein, refers to a film allowing water or solvent to pass through it, but is impermeable to the dissolved active ingredient and other excipients, thereby preventing the passage of dissolved active ingredient and other excipients through it. The semi-permeable film may include film-forming agents, for example, polyvinylalcohol, hydroxypropyl starch, hydroxyethyl starch, hydroxypropyl cellulose, hydroxypropyl methyl cellulose, hydroxypropyl methylcellulose phthalate, hydroxypropyl methylcellulose acetate succinate, methyl cellulose, cellulose acetate, and polyacrylic resin; pore-forming agents such as polyethylene glycol, hydroxypropyl cellulose, micronized sugar, sodium chloride, mannitol, and sorbitol; or plasticizers such as triethyl citrate, castor oil, dibutyl sebacate, phthalates, polyethylene glycol, glycerol, and poloxamer; and combinations thereof.

Preferred examples of solvents used for preparing the coating solution of the semi-permeable film may include, but are not limited to, methylene chloride, isopropyl alcohol, acetone, propylene glycol, methanol, ethanol, chloroform, ether, water, and combinations thereof.

Preferred examples of glidants and lubricants may include, but are not limited to, sodium lauryl sulfate, talc, magnesium stearate, sodium stearyl fumarate, stearic acid, glyceryl behenate, hydrogenated vegetable oil, zinc stearate, and colloidal silicon dioxide.

The gastro-retentive solid oral dosage form of the present invention may be prepared by conventional processes of wet granulation, dry granulation, or direct compression. The processes may also involve coating of the dosage form with functional coatings such as a semi-permeable film coating.

The invention may be further illustrated by the following examples, which are for illustrative purposes only and should not be construed as limiting the scope of the invention in any way.

EXAMPLES

Example 1

Density Based Gastro-Retentive Tablets

| S. No. | Ingredients | Quantity (% w/w) |
|---|---|---|
| 1 | Nilotinib | 50.00 |
| 2 | Acidifying Agent (Fumaric acid, citric acid, tartaric acid, or amino acid) | 5.00 |
| 3 | Microcrystalline Cellulose | 29.25 |
| 4 | Hypromellose | 10.00 |
| 5 | Polyvinylpyrrolidone | 2.50 |
| 6 | Carbomer Homopolymer Type A | 1.25 |
| 7 | Colloidal Silicon Dioxide | 1.00 |
| 8 | Magnesium Stearate | 1.00 |

Manufacturing Procedure:
1) Sift nilotinib, the acidifying agent, microcrystalline cellulose, hypromellose, polyvinylpyrrolidone, carbomer homopolymer type A, and colloidal silicon dioxide through a BSS #18 sieve.
2) Sift magnesium stearate through a BSS #60 sieve.
3) Blend the materials of step 1 in a low shear blender for 15 minutes.
4) Blend the materials of step 2 and step 3 in a low shear blender for 10 minutes.
5) Compress the blend of step 4 into tablets using suitable tooling.

Example 2

Gas Generating Gastro-Retentive Tablets

| S. No. | Ingredients | Quantity (% w/w) |
|---|---|---|
| 1 | Nilotinib | 38.00 |
| 2 | Acidifying Agent (Fumaric acid, citric acid, tartaric acid, or amino acid) | 4.00 |
| 3 | Sodium Bicarbonate | 8.00 |
| 4 | Microcrystalline Cellulose | 10.00 |
| 5 | Lactose Anhydrous | 8.00 |
| 6 | Xanthan Gum | 30.00 |
| 7 | Colloidal Silicon Dioxide | 1.00 |
| 8 | Magnesium Stearate | 1.00 |

Manufacturing Procedure:
1) Sift nilotinib, the acidifying agent, sodium bicarbonate, microcrystalline cellulose, lactose anhydrous, xanthan gum, and colloidal silicon dioxide through a BSS #18 sieve.
2) Sift magnesium stearate through a BSS #60 sieve.
3) Blend the materials of step 1 in a low shear blender for 15 minutes.
4) Blend the materials of step 2 and step 3 in a low shear blender for 10 minutes.
5) Compress the blend of step 4 into tablets using a suitable tooling.

Example 3

Size Based Gastro-Retentive Osmotic Tablets

| S. No. | Ingredients | Quantity (% w/w) |
|---|---|---|
| 1 | Nilotinib | 46.40 |
| 2 | Acidifying Agent (Fumaric acid, citric acid, tartaric acid, or amino acid) | 11.60 |
| 3 | Lactose Monohydrate | 21.46 |
| 4 | Sodium Chloride | 5.80 |
| 5 | Colloidal Silicon Dioxide | 0.87 |
| 6 | Magnesium Stearate | 0.87 |
| 7 | Hypromellose | 3.00 |
| 8 | Cellulose Acetate | 9.90 |
| 9 | Polyethylene Glycol | 0.10 |

Manufacturing Procedure:
1) Sift nilotinib, the acidifying agent, sodium chloride, lactose monohydrate, and colloidal silicon dioxide through a BSS #18 sieve.
2) Sift magnesium stearate through a BSS #60 sieve.
3) Blend the materials of step 1 in a low shear blender for 15 minutes.
4) Blend the materials of step 2 and step 3 in a low shear blender for 10 minutes.
5) Compress the blend of step 4 into tablets using a suitable tooling.
6) Dissolve hypromellose in water.
7) Coat the tablets of step 5 with the solution of step 6.
8) Dissolve cellulose acetate and polyethylene glycol in an acetone and water mixture.
9) Coat the tablets of step 7 with the solution of step 8.
10) Cure the tablets of step 9 for a period of 24 hours at 40° C.
11) Drill the tablets of step 10 with one hole on one side or one hole on both sides using a laser beam to a particular diameter and depth.

Example 4

Gastro Floating Capsules

| S. No. | Ingredients | Quantity (% w/w) |
|---|---|---|
| 1 | Nilotinib | 70.0 |
| 2 | Lactose Monohydrate | 10.0 |
| 3 | Gelatin/HPMC Capsule | 10.0 |
| 4 | Cellulose Acetate/Ethyl cellulose | 9.0 |
| 5 | Polyethylene Glycol | 1.0 |

Manufacturing Procedure:
Preparation of Capsules:
1) Capsules may be prepared by any one of the following methods:
   a. Capsules may be filled with nilotinib.
   b. Capsules may be filled with nilotinib and lactose as granules or powder.
   c. Nilotinib and lactose mini-tablets may be filled into the capsules.
2) Prepare gelatin solution and use it to band seal the capsules of step 1.
Coating of Capsules:
3) Coat the capsules of step 2 with cellulose acetate or ethyl cellulose solution containing polyethylene glycol.

We claim:

1. A gastro-retentive tablet which comprises nilotinib or a salt thereof, at least one rate-controlling polymer which is a swelling agent, and other pharmaceutically acceptable excipients wherein the gastroretentive action of the tablet is based on swelling mechanism.

2. The gastro-retentive tablet of claim 1, wherein the tablet further comprises an acidifying agent.

3. The gastro-retentive tablet of claim 1, wherein the tablet is administered once daily or twice daily.

4. The gastro-retentive tablet of claim 1, wherein the other pharmaceutically acceptable excipients are selected from diluents, matrix forming agents, disintegrants, binding agents, gas-generating agents, semi-permeable film-forming agents, glidants, and lubricants.

5. The gastro-retentive tablet of claim 4, wherein the gas generating agent is selected from alkali metal carbonates and bicarbonates.

6. The gastro-retentive tablet of claim 5, wherein the tablet containing the gas generating agent is uncoated.

7. The gastro-retentive tablet of claim 5, wherein the gastro-retentive action of the solid dosage form is based on the mechanism of floatation.

8. A gastro-retentive tablet which comprises nilotinib or a salt thereof, at least one rate-controlling polymer, one or more osmogen agents, and other pharmaceutically acceptable excipients wherein the tablet is coated with a semi-permeable film and at least one hole or opening through the semi-permeable film for drug release.

9. A gastro-retentive tablet which comprises nilotinib or a salt thereof, at least one rate-controlling polymer, one or more osmogen agents, and other pharmaceutically acceptable excipients wherein the tablet is coated with a semi-permeable film comprising a film forming agent and a pore forming agent.

10. A gastro-retentive capsule comprising nilotinib and a diluent in the form of a powder, granules, or minitablet in the capsule wherein the capsule has an outer coating in the form of a semi-permeable film comprising a film forming agent and a pore forming agent and the capsule does not disintegrate until the drug is released.

* * * * *